(12) United States Patent
Lawrence et al.

(10) Patent No.: US 9,456,867 B2
(45) Date of Patent: Oct. 4, 2016

(54) OPEN IRRIGATED ABLATION CATHETER

(71) Applicant: BOSTON SCIENTIFIC SCIMED, INC., Maple Grove, MN (US)

(72) Inventors: David Lawrence, Mountain View, CA (US); Eliza Lawrence, Mountain View, CA (US); Isaac J. Kim, San Jose, CA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 289 days.

(21) Appl. No.: 14/209,779

(22) Filed: Mar. 13, 2014

(65) Prior Publication Data

US 2014/0276758 A1    Sep. 18, 2014

Related U.S. Application Data

(60) Provisional application No. 61/793,345, filed on Mar. 15, 2013.

(51) Int. Cl.
| A61B 18/14 | (2006.01) |
| A61B 18/18 | (2006.01) |
| A61B 5/042 | (2006.01) |
| A61B 18/00 | (2006.01) |

(52) U.S. Cl.
CPC ........... *A61B 18/1492* (2013.01); *A61B 5/042* (2013.01); *A61B 18/18* (2013.01); *A61B 2018/00029* (2013.01); *A61B 2018/00351* (2013.01); *A61B 2018/00839* (2013.01)

(58) Field of Classification Search
CPC .............. A61B 2218/002; A61B 2018/00029; A61M 2025/0073
See application file for complete search history.

(56) References Cited

U.S. PATENT DOCUMENTS

| 4,636,313 | A | | 1/1987 | Vaillancourt |
| 5,238,004 | A | | 8/1993 | Sahatjian et al. |
| 5,413,107 | A | | 5/1995 | Oakley et al. |
| 5,458,597 | A | | 10/1995 | Edwards et al. |
| 5,545,161 | A | * | 8/1996 | Imran ................ A61B 18/1492 606/41 |
| 5,584,872 | A | * | 12/1996 | LaFontaine ........ A61B 18/1485 607/116 |

(Continued)

FOREIGN PATENT DOCUMENTS

| EP | 2380519 A1 | 10/2011 |
| WO | 2009048824 A1 | 4/2009 |

(Continued)

OTHER PUBLICATIONS

International Preliminary Report on Patentability issued in PCT/US2013/073461, maiied Jun. 18, 2015, 11 pages.

(Continued)

*Primary Examiner* — Jocelyn D Ram
(74) *Attorney, Agent, or Firm* — Faegre Baker Daniels LLP

(57) ABSTRACT

Medical devices and methods for using medical devices are disclosed. An example medical device may include an open-irrigated ablation catheter. The open-irrigated ablation catheter may include a catheter body, an electrode tip body with irrigation ports at a distal end, and a coolant conduit. The distal end of the coolant conduit may extend into a proximal portion of the electrode tip body. Fluid flow from the coolant conduit may be diverted proximally and/or towards the wall of the electrode tip body by one or more openings proximal of a closed distal end of the conduit or by a structure blocking and diverting flow from an open distal end of the conduit.

19 Claims, 3 Drawing Sheets

(56) References Cited

U.S. PATENT DOCUMENTS

| | | | |
|---|---|---|---|
| 5,643,197 A | 7/1997 | Brucker et al. | |
| 5,688,267 A | 11/1997 | Panescu et al. | |
| 5,772,609 A | 6/1998 | Nguyen et al. | |
| 5,779,699 A | 7/1998 | Lipson | |
| 5,871,525 A | 2/1999 | Edwards et al. | |
| 5,895,355 A | 4/1999 | Schaer | |
| 5,932,035 A | 8/1999 | Koger et al. | |
| 6,013,052 A | 1/2000 | Durman et al. | |
| 6,053,912 A | 4/2000 | Panescu et al. | |
| 6,120,476 A | 9/2000 | Fung et al. | |
| 6,139,510 A | 10/2000 | Palermo | |
| 6,287,301 B1 | 9/2001 | Thompson et al. | |
| 6,508,803 B1 | 1/2003 | Horikawa et al. | |
| 7,628,788 B2* | 12/2009 | Datta | A61B 18/1492 606/41 |
| 7,914,528 B2* | 3/2011 | Wang | A61B 18/1492 606/41 |
| 8,128,620 B2 | 3/2012 | Wang et al. | |
| 8,273,082 B2 | 9/2012 | Wang et al. | |
| 8,517,999 B2* | 8/2013 | Pappone | A61M 25/003 604/264 |
| 2003/0004506 A1* | 1/2003 | Messing | A61B 18/1492 606/41 |
| 2003/0009094 A1 | 1/2003 | Segner et al. | |
| 2005/0203410 A1 | 9/2005 | Jenkins | |
| 2006/0074444 A1 | 4/2006 | Lin et al. | |
| 2006/0184165 A1* | 8/2006 | Webster, Jr. | A61B 18/1492 606/41 |
| 2007/0270791 A1 | 11/2007 | Wang et al. | |
| 2008/0071267 A1 | 3/2008 | Wang et al. | |
| 2008/0091193 A1 | 4/2008 | Kauphusman et al. | |
| 2008/0147060 A1 | 6/2008 | Choi | |
| 2008/0161789 A1 | 7/2008 | Thao et al. | |
| 2008/0161792 A1* | 7/2008 | Wang | A61B 18/1492 606/41 |
| 2008/0161795 A1* | 7/2008 | Wang | A61B 18/1492 606/41 |
| 2008/0200801 A1 | 8/2008 | Wildes et al. | |
| 2008/0243214 A1 | 10/2008 | Koblish | |
| 2008/0249522 A1 | 10/2008 | Pappone et al. | |
| 2009/0012517 A1 | 1/2009 | de la Rama et al. | |
| 2009/0093810 A1 | 4/2009 | Subramaniam et al. | |
| 2009/0093811 A1* | 4/2009 | Koblish | A61B 18/1492 606/41 |
| 2009/0125016 A1* | 5/2009 | Wang | A61B 18/1492 606/41 |
| 2009/0143779 A1 | 6/2009 | Wang et al. | |
| 2009/0171345 A1 | 7/2009 | Miller et al. | |
| 2009/0177193 A1 | 7/2009 | Wang et al. | |
| 2009/0259222 A1 | 10/2009 | Wang et al. | |
| 2010/0114093 A1 | 5/2010 | Mahapatra et al. | |
| 2010/0168728 A1 | 7/2010 | Wang et al. | |
| 2010/0249601 A1 | 9/2010 | Courtney | |
| 2010/0331658 A1* | 12/2010 | Kim | A61B 18/18 600/373 |
| 2011/0009857 A1* | 1/2011 | Subramaniam | A61B 18/1492 606/33 |
| 2011/0022041 A1 | 1/2011 | Ingle et al. | |
| 2011/0092969 A1 | 4/2011 | Wang et al. | |
| 2011/0144657 A1 | 6/2011 | Fish et al. | |
| 2011/0201973 A1 | 8/2011 | Stephens et al. | |
| 2011/0224667 A1 | 9/2011 | Koblish et al. | |
| 2011/0257523 A1 | 10/2011 | Hastings et al. | |
| 2011/0264089 A1* | 10/2011 | Zirkle | A61B 5/042 606/41 |
| 2011/0270046 A1 | 11/2011 | Paul et al. | |
| 2011/0270246 A1* | 11/2011 | Clark | A61B 18/1492 606/41 |
| 2012/0017287 A1 | 1/2012 | Bumiller et al. | |
| 2012/0029504 A1 | 2/2012 | Afonso et al. | |
| 2012/0029511 A1 | 2/2012 | Smith et al. | |
| 2012/0035466 A1 | 2/2012 | Tegg | |
| 2012/0035539 A1* | 2/2012 | Tegg | A61B 18/1492 604/95.01 |
| 2012/0035605 A1* | 2/2012 | Tegg | A61B 18/1492 606/41 |
| 2012/0046610 A1* | 2/2012 | Rankin | A61M 25/0067 604/122 |
| 2012/0130363 A1 | 5/2012 | Kim et al. | |
| 2012/0150175 A1 | 6/2012 | Wang et al. | |
| 2012/0165812 A1* | 6/2012 | Christian | A61B 18/1492 606/41 |
| 2012/0172871 A1 | 7/2012 | Hastings et al. | |
| 2012/0221001 A1 | 8/2012 | Tegg et al. | |
| 2013/0137980 A1 | 5/2013 | Waters et al. | |
| 2014/0187893 A1* | 7/2014 | Clark | A61B 5/042 600/373 |
| 2014/0276759 A1* | 9/2014 | Kim | A61B 18/1492 606/33 |

FOREIGN PATENT DOCUMENTS

| | | |
|---|---|---|
| WO | 2009048943 A1 | 4/2009 |
| WO | 2014151876 A1 | 9/2014 |

OTHER PUBLICATIONS

International Preliminary Report on Patentabiiity issued in PCT/US2014/026509, mailed Sep. 24, 2015, 12 pages.

International Preliminary Report on Patentabiiity issued in PCT/US2014/026602, mailed Sep. 24, 2015, 10 pages.

International Search Report arid Written Opinion issued in PCT/US2013/073461, mailed Jun. 6, 2014, 15 pages.

International Search Report and Written Opinion issued in PCT/US2014/026509, mailed Nov. 11, 2014, 16 pages.

International Search Report and Written issued in PCT/US2014/026602, mailed Jun. 25, 2014, 12 pages.

\* cited by examiner

OPEN IRRIGATED ABLATION CATHETER

CROSS-REFERENCE TO RELATED APPLICATIONS

This application claims priority under 35 U.S.C. §119 to U.S. Provisional Application Ser. No. 61/793,345, filed Mar. 15, 2013, the entirety of which is incorporated herein by reference.

TECHNICAL FIELD

The present disclosure pertains to medical devices. More particularly, the present disclosure pertains to systems, devices and methods related to open-irrigated catheters used to perform ablation functions.

BACKGROUND

Aberrant conductive pathways disrupt the normal path of the heart's electrical impulses. For example, conduction blocks can cause the electrical impulse to degenerate into several circular wavelets that disrupt the normal activation of the atria or ventricles. The aberrant conductive pathways create abnormal, irregular, and sometimes life-threatening heart rhythms called arrhythmias. Ablation is one way of treating arrhythmias and restoring normal contraction. The sources of the aberrant pathways (called focal arrhythmia substrates) are located or mapped using mapping electrodes situated in a desired location. After mapping, the physician may ablate the aberrant tissue. In radio frequency (RF) ablation, RF energy is directed from the ablation electrode through tissue to an electrode to ablate the tissue and form a lesion.

Heat is generated during the RF ablation process, and this heat may cause a thrombus (blood clot). Some ablation catheter systems have been designed to cool the electrode and surrounding tissue. Alternative or new designs or methods for cooling the electrode and/or surround tissue are desirable.

BRIEF SUMMARY

This disclosure provides design, materials, methods of making, and use alternatives for medical devices. For example, some embodiments relate to open-irrigated catheter systems that pump a cooling fluid, such as a saline solution, through a lumen in the body of the catheter, out through the ablation electrode, and into surrounding tissue. The cooling fluid cools the ablation electrode and surrounding tissue, thus reducing the likelihood of a thrombus, preventing or reducing impedance rise of tissue in contact with the electrode tip, and increasing energy transfer to the tissue because of the lower tissue impedance.

An example medical device may include an open-irrigated ablation catheter system. The open-irrigated ablation catheter system may include a catheter body with a distal end, an electrode tip body with a distal end and a proximal end configured for connection to a distal end of the catheter body. The electrode tip body may include a wall defining an open interior region with one or more irrigation ports. The wall may be conductive for delivering radio frequency (RF) energy for an RF ablation procedure. The irrigation ports may be in fluid communication with the open interior region to allow fluid to flow from the open interior region through the irrigation ports. The open-irrigated ablation catheter system may include a coolant conduit disposed within the catheter body with a fluid directing mechanism at a distal end thereof configured to direct fluid laterally towards the wall. In some examples, the distal end of the coolant conduit may be closed. In some examples, the distal end of the coolant conduit may be open. In some examples, the fluid directing mechanism may include one or more side openings proximal of the distal end of the coolant conduit. In some examples, the fluid directing mechanism may include a blocking member spaced from an open end of the coolant conduit.

The open-irrigated catheter system may include a distal insert positioned within the electrode tip body, separating the open interior region into a distal fluid reservoir and a proximal fluid reservoir. The distal insert may have an opening connecting the distal and proximal fluid reservoirs. The distal end of the coolant conduit may be positioned in the proximal fluid reservoir, and the one or more irrigation port may be disposed in the distal fluid reservoir.

Another example open-irrigated ablation catheter system may include a catheter body, an electrode tip body, a coolant conduit, and a blocking member. The electrode tip body may have a proximal end configured for connection to a distal end of the catheter body. The electrode tip body may have a wall defining an open interior region and one or more irrigation ports. The irrigation ports may be in fluid communication with the open interior region to allow fluid to flow from the open interior region through the irrigation ports. The wall may be conductive for delivering radio frequency (RF) energy for an RF ablation procedure. The open-irrigated ablation catheter system may also include a coolant conduit disposed within the catheter body. A distal end of the coolant conduit may extend distal of the distal end of the catheter body, and the distal end of the coolant conduit may be open. The open-irrigated ablation catheter system may also include a blocking member spaced from the distal end of the coolant conduit, and the blocking member may be configured to interrupt distal flow of fluid from the coolant conduit and redirect flow laterally.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
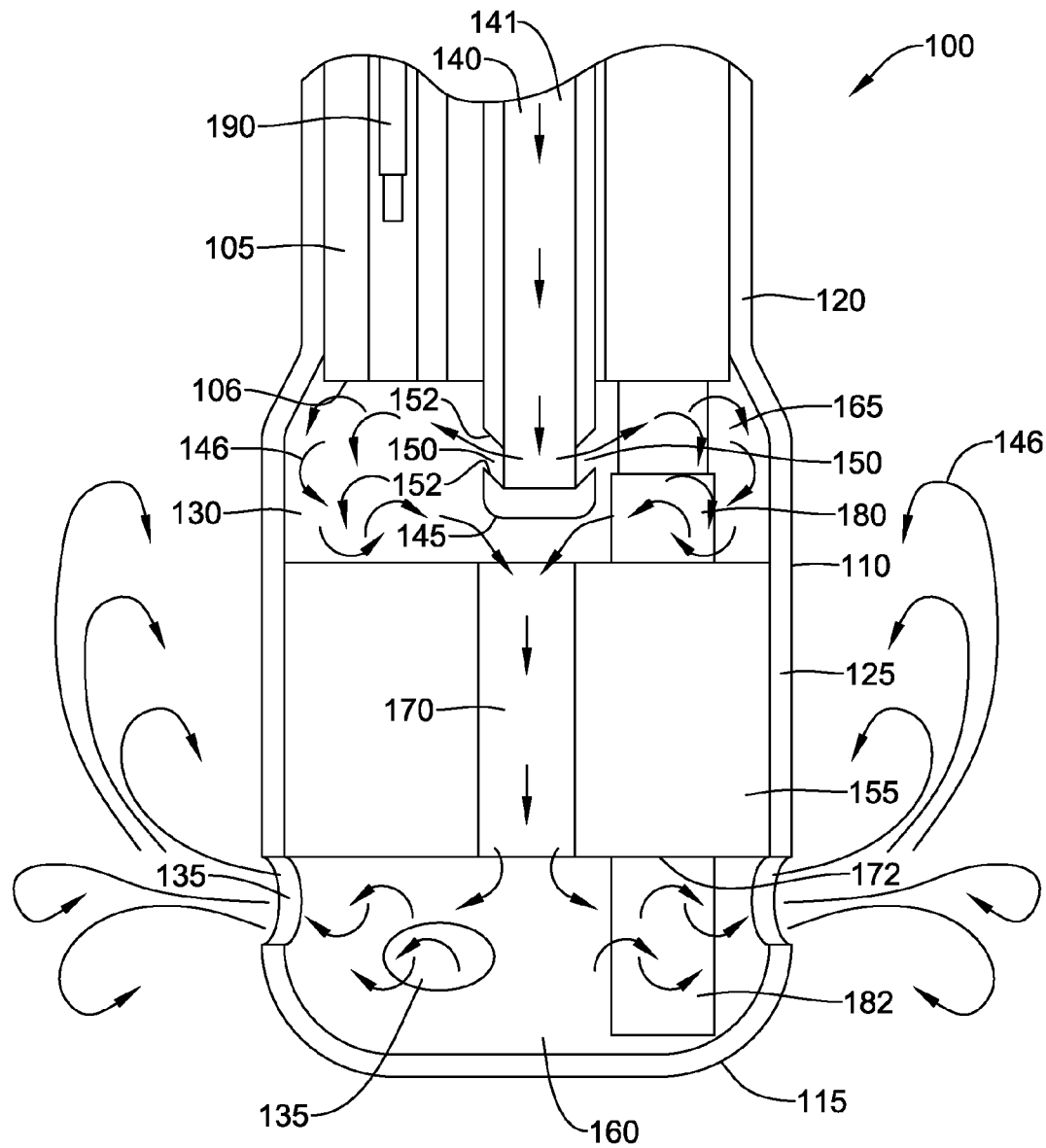
FIG. 1 is a cross-sectional side view of an open-irrigated catheter electrode tip according to an embodiment of the present subject matter.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

This present subject matter generally relates to an open-irrigated radiofrequency (RF) ablation catheter system. In some embodiments, the catheter may be referred to as a hybrid catheter as it can be used simultaneously for both localized mapping and ablation functions. However, not all embodiments would necessarily include both the mapping and ablation functions, and may instead incorporate only one or the other function. The hybrid catheter is configured to provide localized, high resolution ECG signals during ablation. The localized mapping enables the mapping to be more precise than that which can be achieved with conventional ablation catheters. The hybrid catheter has an open-irrigated catheter design. A cooling fluid, such as a saline, is delivered through the catheter to the catheter tip, where the fluid exits through irrigation ports to cool the electrode and surrounding tissue. Clinical benefits of such a catheter include, but are not limited to, controlling the temperature and reducing coagulum formation on the tip of the catheter, preventing impedance rise of tissue in contact with the catheter tip, and maximizing potential energy transfer to the tissue. Additionally, the localized intra cardiac electrical activity can be recorded in real time or near-real time right at the point of energy delivery.

Some embodiments may be used within body lumens, chambers or cavities for diagnostic or therapeutic purposes in those instances where access to interior bodily regions is obtained through, for example, the vascular system or alimentary canal and/or with minimally invasive surgical procedures. For example, some embodiments herein have application in the diagnosis and treatment of arrhythmia conditions within the heart. Some embodiments herein also have application in the diagnosis or treatment of ailments of the gastrointestinal tract, prostrate, brain, gall bladder, uterus, and other regions of the body. With regard to the treatment of conditions involving the heart, some embodiments can be used to create lesions to treat atrial fibrillation, atrial flutter and ventricular tachycardia. Additionally, some embodiments can be used to modulate, block, or ablate nerve bodies in the treatment of neural structures. For example, some embodiments have application in the treatment of congestive heart failure, hypertension, and other cardio-renal diseases. With regard to the treatment of cardio-renal diseases, some embodiments can be used to modulate neural function of the renal nerve.

If near laminar flow conditions are at the exit ports of an open-irrigated catheter, stable eddy currents may be formed around the electrode. Under these conditions, there could be hot spots by the ablation electrode, particularly around the proximal part of the electrode. If these stable eddy currents trap blood platelets near the electrode, and if these trapped platelets are activated due to heat and shear force, a thrombus could potentially form. Near laminar flow of cooling fluid from the irrigation ports tends to cause the cooling fluid to flow away from the ablation electrode and the tissue near the ablation site, potentially causing uneven cooling and localized hot spots along the ablation electrode.

The present subject matter may provide systems and methods for cooling the ablation electrode and the surrounding tissue in a more uniform manner. An open-irrigated RF ablation catheter is designed to divert the initial flow of cooling fluid within the electrode to improve the uniformity of cooling. The risk of thrombus formation significantly decreases using diverted flow of cooling fluid to uniformly cool the electrode. Although the present embodiments are not so limited, the exemplary catheter is configured for use within the heart and, accordingly, is about 5 French to about 11 French (about 1.67 mm to about 3.67 mm) in diameter. The wall thickness of the exemplary electrode tip may be about 0.05 mm to about 0.3 mm. The portion of the catheter that is inserted into the patient is typically from about 60 to 160 cm in length. The length and flexibility of the catheter allow the catheter to be inserted into a main vein or artery (typically the femoral vein), directed into the interior of the heart, and then manipulated such that the desired electrode(s) contact the target tissue. Fluoroscopic imaging may be used to provide the physician with a visual indication of the location of the catheter.

Figure 2:
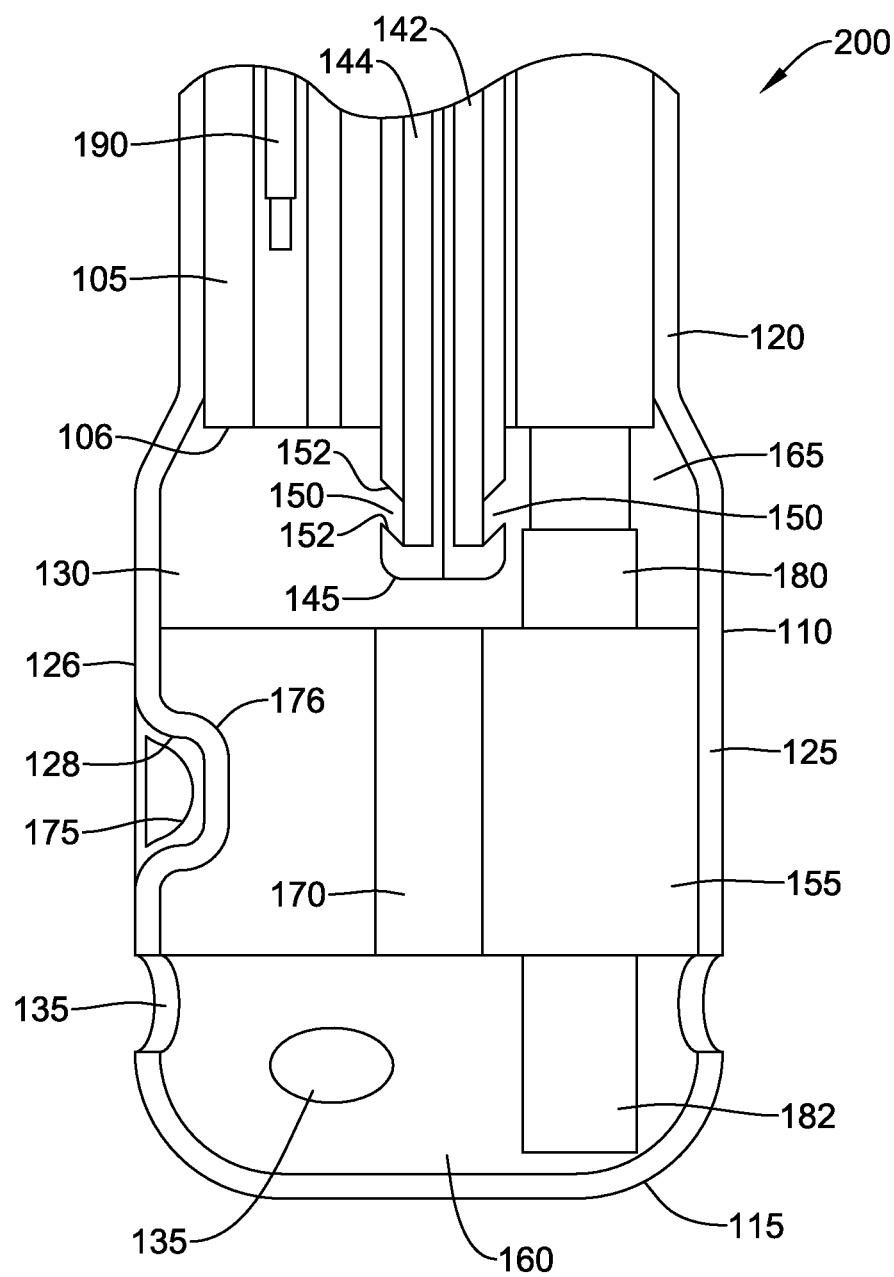
FIG. 2 is a cross-sectional side view of an open-irrigated catheter electrode tip according to another embodiment of the present subject matter.
Figure 3:
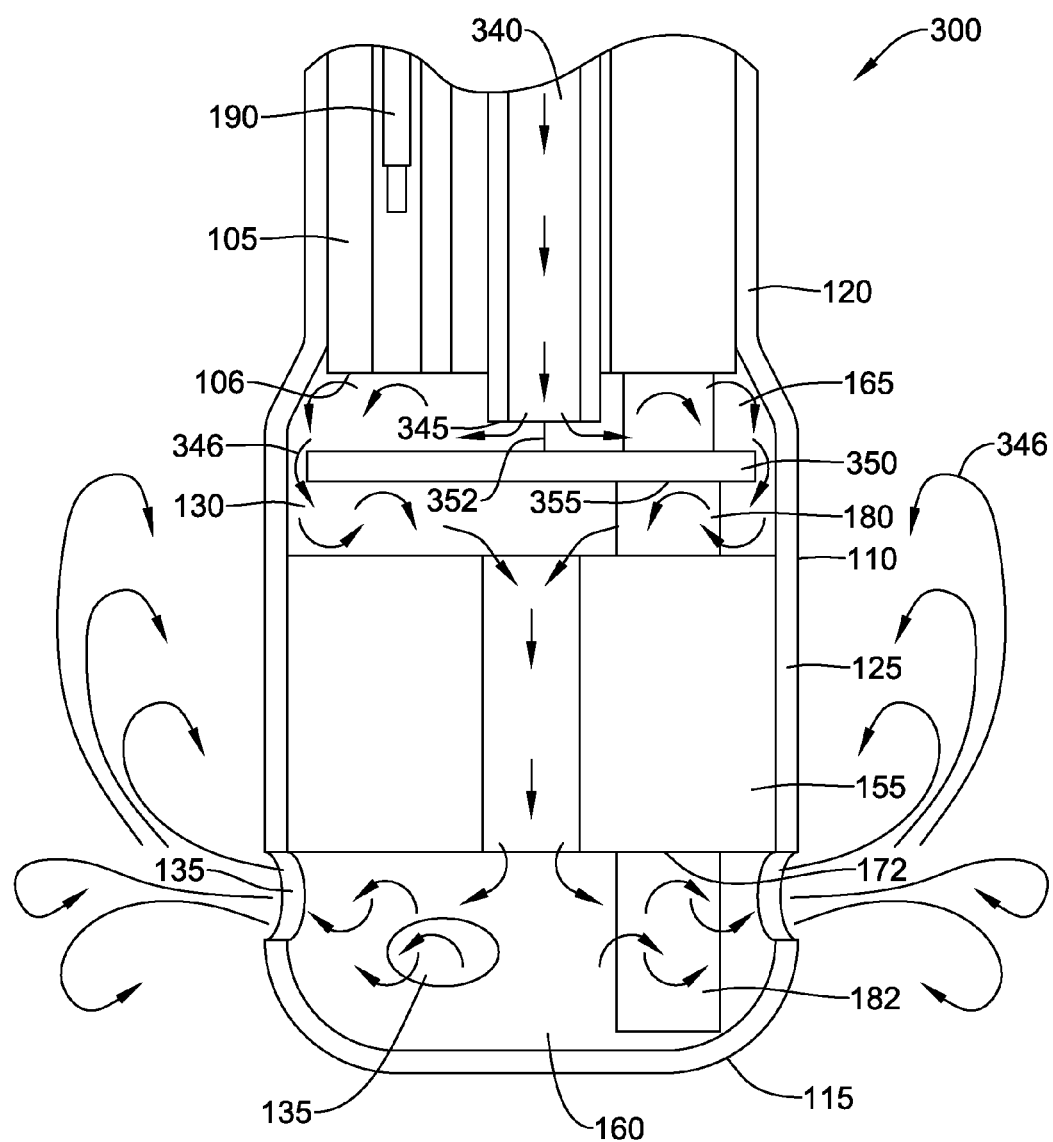
FIG. 3 is a cross-sectional side view of an open-irrigated catheter electrode tip according to yet another embodiment of the present subject matter.

With respect to steering, the exemplary catheter apparatus 100 illustrated in FIGS. 1-3 may be provided with a conventional steering mechanism. For example, the catheter may include a steering wire (not shown) slidably disposed within the catheter body, or a steering center support and steering wire arrangement (not shown). A steering center support with a pair of adjacent steering wires may extend through the catheter body to a handle (not shown), which is also configured for steering. Additional details concerning this type of steering arrangement may be found in, for example, U.S. Pat. Nos. 5,871,525 and 6,287,301, which are hereby incorporated by reference. Other suitable steering arrangements are disclosed in U.S. Pat. Nos. 6,013,052 and 6,287,301, which are hereby incorporated by reference. Nevertheless, it should be noted that the present inventions are not limited to steerable catheter apparatus, or to any particular type of steering arrangement in those catheter apparatus which are steerable.

FIG. 1 illustrates the distal end of an open-irrigated catheter system 100 with a catheter body 105 and an electrode tip 110. The electrode tip 110 is generally hollow with a closed distal end 115, an open interior region 130, and an open proximal end 120. The distal end 115 may be planar. The open proximal end 120 is configured for connection with the distal end 106 of the catheter body 105. In the embodiment illustrated in the figures, the proximal end 120 is shown outside of the catheter body 105. However, other embodiments are not so limited, and the proximal end 120 may be configured to fit within the distal end 106 of the catheter body 105. It should be noted that in the embodiment shown, there are no holes in the distal end 115 wall of the exemplary electrode tip 110 for fluid cooling and/or passage of a temperature sensor that is aligned with the outer surface of the electrode. Such holes may create regions of high current density and regions of high current density near the center of the electrode tip would work against efforts to move current to the outer perimeter of the electrode tip. However, the present disclosure is not so limited, and other arrangements are contemplated, for example, embodiments with holes or openings in the distal end 115. The catheter body 105 has a lumen therein to receive an RF wire 190 used to deliver the RF energy from an RF generator (not shown) to the electrode. At least one coolant conduit 140 defining a lumen 141 is disposed within the catheter body 105, extending distal of the catheter body distal end 106 into the open interior region 130.

A distal insert 155 divides the open interior region 130 of the electrode tip 110 into a distal fluid reservoir 160 and a proximal fluid reservoir 165, each of which act as cooling chambers. The distal insert 155 may be a thermal mass. At least one opening 170 connects the distal fluid reservoir 160 and the proximal fluid reservoir 165. In the embodiment illustrated in the figures, a single opening 170 is shown. However, other embodiments are not so limited, and more than one opening 170 may extend through the distal insert 155, providing multiple pathways for fluid to travel from the proximal fluid reservoir 165 to the distal fluid reservoir 160. One or more irrigation ports 135 through the wall 125 of the electrode tip near the distal end 115 allow fluid to exit the device. When more than one irrigation port is present, the irrigation ports 135 may be equally spaced around the circumference of the electrode tip. However, the present subject matter is not limited to equally-spaced irrigation ports or to a particular number of irrigation ports. The system can be designed with other numbers and arrangements of irrigation ports.

A plurality of irrigation ports 135 or exit ports are shown near the distal end 115 of the electrode tip 110 in FIG. 1. By way of example and not limitation, some embodiments have irrigation ports with a diameter approximately within a range of 0.01 to 0.02 inches (0.0254 to 0.0508 cm). Fluid, such as a saline solution, flows from the coolant conduit 140 into the proximal fluid reservoir 165, through opening 170 into the distal fluid reservoir 160, and through irrigation ports 135 to the exterior of the catheter. This fluid is used to cool the ablation electrode tip and/or the tissue near the electrode. This temperature control may reduce coagulum formation on the tip of the catheter, may prevent impedance rise of tissue in contact with the catheter tip, and may increase energy transfer to the tissue because of the lower tissue impedance.

The cooling fluid may cool both the electrode tip 110 and the tissue adjacent to the perimeter of the electrode tip. For example, the cooling fluid draws heat from the electrode tip 110 (including the thermal mass distal insert 155) and reduces the temperature of the electrode. The presence of the proximal fluid reservoir 165 and distal fluid reservoir 160 augments the fluid cooling because the fluid circulates within the proximal fluid reservoir 165 prior to entering the distal fluid reservoir 160, and circulates within the distal fluid reservoir 160 prior to exiting the electrode tip 110 by way of the irrigation ports 135. The decrease in electrode and tissue temperature reduces the likelihood that the tissue in contact with the electrode tip 110 will char and/or that coagulum will form on the surface of the electrode tip. As such, the amount of energy supplied to the tissue may be increased, and the energy is transferred to the tissue more efficiently, as compared to an electrode that is not configured for fluid cooling. This results in the formation of larger and deeper lesions. In addition to cooling tissue adjacent to the electrode tip 110, fluid that exits the electrode tip sweeps biological material such as blood and tissue away from the electrode, further reducing the likelihood of coagulum formation.

Fluid flowing along the pathway from the coolant conduit 140 through the proximal fluid reservoir 165, opening 170, distal fluid reservoir 160, and out the irrigation ports 135 is used to provide targeted cooling of portions of the electrode tip. In the illustrated embodiment, the hollow electrode tip 110 has a generally cylindrical shape. By way of an example and not limitation, some embodiments of electrode tip have a diameter in the range of about 0.08 to 0.1 inches (about 0.2032 to 0.254 cm), has a length in the range of about 0.2 to 0.3 inches (about 0.508 to 0.762 cm), and has an exterior wall with a thickness in the range of about 0.003 to 0.004 inches (0.00762 to 0.01016 cm). The catheter system may include a temperature sensor mounted within the electrode tip 110. In the illustrated embodiment, the temperature sensor is a thermocouple 180 that extends through the catheter body 105 and through an opening 172 in the distal insert 155, allowing a distal end 182 of the thermocouple to be positioned in the distal fluid reservoir 160.

The proximal and distal fluid reservoirs 165, 160, respectively, the coolant conduit 140, the opening 170 in the distal insert, and the irrigation ports 135 are designed with appropriate dimensions and geometry with respect to each other to change the laminar flow of fluid within the coolant conduit 140 into a turbulent fluid flow, indicated at 146, as the pressurized cooling fluid flows out of the coolant conduit 140, through the proximal fluid reservoir 165, through the opening 170 in the distal insert, through the distal fluid reservoir 160, and out the irrigation ports 135. Coolant is pumped at high pressure in the catheter. When it enters the proximal fluid reservoir 165, the fluid circulates within the reservoir to cool the proximal portion of the electrode tip and mitigate overheating (edge effect). Laminar flow is further disturbed as the coolant is forced into the distal fluid reservoir 160. The turbulence increases as the coolant exits through the irrigation ports. The edges of the irrigation ports 135 may be purposely left rough and ragged. The distal end 115 of the electrode tip is a relatively flat wall. The combination of these factors may cause the fluid exiting the irrigation ports to create turbulence around the entire electrode body, encouraging a more uniform cooling of the electrode body and the dilution of the blood in the vicinity of the ablation electrode. Additionally, the irrigation ports 135 may be individually configured and arranged to encourage the fluid to flow out of the electrode tip 110 laterally as well as at an angle toward the proximal end of the electrode to cause the cooling fluid to flow, in a turbulent manner, as indicated at 146, towards the proximal end of the electrode exterior as well as at the distal end of the electrode.

The open-irrigated catheter system 100 may include a fluid directing mechanism configured to redirect fluid flow from the distal end 145 of the coolant conduit 140 laterally towards the side wall 125 and/or the proximal end 120 of the electrode tip 110. In some embodiments, the fluid directing mechanism includes one or more side openings 150 proximal of the distal end 145 of the coolant conduit 140, as shown in FIG. 1. In some embodiments, the fluid directing mechanism includes a blocking member 350 spaced from an open distal end 345 of the coolant conduit 340, as shown in FIG. 3.

The distal end 145 of the coolant conduit 140 may provide the fluid directing mechanism. The distal end 145 may be designed to cause the cooling fluid to be diverted towards the proximal end 120 of the electrode tip 110 and the distal end 106 of the catheter body 105, where hot spots may otherwise develop. For example, as shown in FIG. 1, the distal end 145 of the coolant conduit 140 may be closed with one or more openings 150 through the side wall of the coolant conduit 140. The side openings 150 may be located proximal of the closed distal end 145. The openings 150 may be configured to direct cooling fluid towards the proximal end 120 of the electrode tip 110, laterally towards a side wall 125 of the electrode tip 110, or both. In some embodiments, the openings 150 in the coolant conduit 140 include angled surfaces 152 configured to direct turbulent coolant fluid flow, indicated at 146, toward the proximal end 120 of the electrode tip 110 and the distal end 106 of the catheter body 105. In some embodiments, a plurality of openings 150 may extend circumferentially around the coolant conduit 140. The openings 150 may each have angled surfaces 152 where the angles differ from opening to opening. Alternatively, the openings may be angled to the same degree. The openings 150 may be arranged in rows or any other pattern.

The coolant conduit 140 may have multiple lumens. For example, FIG. 2 is a cross-sectional side view of catheter system 200. Here it can be seen that coolant conduit 140 includes a first lumen 142 and a second lumen 144. The catheter system 200 may include any number of additional lumens. Each of the first 142 and second 144 lumens has a closed distal end 145 and at least one opening 150. The opening 150 may include a structure, such as an angled surface 152 configured to direct flow of cooling fluid laterally towards the side wall 125, proximally toward the proximal end 120 of the electrode tip 110, or both. The coolant conduit 140 may have multiple openings 150 in each lumen 142, 144, or each lumen may have a single opening 150. Each opening may be sized and/or angled differently, groups of openings may have similarly sized and/or angled openings, or all of the openings may have the same size and/or angle. The lumens 142, 144 may have different lengths such that the distal ends 145 of the lumens extend into the proximal fluid reservoir 165 in a stepped or staggered orientation. The openings 150 may have the same shape or they may be shaped differently. Additionally, the openings 150 in the lumens 142, 144 may be arranged in any pattern around the coolant conduit 140.

As illustrated in the embodiment shown in FIG. 3, in some embodiments, the coolant conduit 340 may have an open distal end 345 and a structure spaced from and blocking the open distal end 345, such as blocking member 350, provides the fluid directing mechanism. In the illustrated embodiment, blocking member 350 is spaced from the open distal end 345 to change the laminar flow within the coolant conduit 340 into a turbulent flow, indicated at 346, and divert fluid flow laterally and/or radially towards the wall 125 of the electrode tip 110. The blocking member 350 may be attached to another structure via an attachment member 352. The blocking member 350 may be attached to the coolant conduit 340, the wall 125 of the electrode tip 110, catheter body 105, or any other part of the catheter system 300. The blocking member 350 may extend generally transverse to a longitudinal axis of the coolant conduit 340. The blocking member 350 may be sized to block at least a portion of the open distal end 345 of the coolant conduit 340. The blocking member 350 may extend beyond the coolant conduit open distal end 345 to block the entire coolant conduit open distal end 345. In some embodiments, the blocking member 350 does not extend to the wall 125, allowing fluid to flow around an edge of the blocking member 350 and into the proximal fluid reservoir 165. In other embodiments, only portions of the blocking member extend to the wall, while still allowing openings for fluid to flow into the proximal fluid reservoir 165. The blocking member 350 causes fluid to circulate at a proximal end of the proximal fluid reservoir, near the junction of the catheter body 105 and the electrode tip 110 before flowing through the opening 170 into the distal fluid reservoir 160 and out the irrigation ports 135. The blocking member 350 may have an opening 355 for receiving the thermocouple 180. The blocking member 350 may be a plate with a shape matching the shape of the electrode tip. For example, the electrode tip 110 may be generally cylindrical and the blocking member may be a circular plate. The blocking member may be sized to extend beyond the outer edge of the coolant conduit 340 but not to the electrode tip wall 125. The distance between the edge of the blocking member 350 and the electrode tip wall 125 may be selected to achieve a desired amount of circulating cooling fluid proximal of the blocking member 350, near the distal end 106 of the catheter body 105 and the proximal end 120 of the electrode tip. In some embodiments, the blocking member may have one or more openings (not shown) to allow fluid to flow through the blocking member as well as around it. The blocking member 350 may extend to the wall 125 of the electrode tip when openings are present in the blocking member. The blocking member 350 may have any shape or thickness and may have a flat proximal surface or may have surface irregularities (not shown) that further disrupt fluid flow across the blocking member. For example, the blocking member may have a wavy, ridged, and/or grooved proximal surface, and/or the blocking member may have protrusions and/or indentations on the proximal surface (not shown). The distal surface of the blocking member may have the same surface characteristics as the proximal surface or the two surfaces may have different surface characteristics.

Any of the catheter systems disclosed herein may include one or more mapping electrodes 175. For example, the distal insert 155 illustrated in the embodiment shown in FIG. 2 includes one or more opening or aperture 176 sized to receive a mapping electrode 175. The electrode tip wall 125 has a corresponding opening 128 in an exterior surface 126 thereof. The mapping electrode 175 may fit within these openings. In one embodiment, the electrode tip includes three mapping electrodes spaced equidistant around the electrode. One, two, or four or more mapping electrodes may also be used and may be arranged in any pattern. These microelectrodes are used in a mapping function to image localized intra-cardiac activity. The device may be used to record high resolution, precise localized electrical activity, to prevent excessive heating of the ablation electrode, to allow greater delivery of power, to prevent the formation of coagulum and to provide the ability to diagnose complex ECG activity. The distal insert 155 may also include openings (not shown) sized to receive electrical conductors (not shown) used to provide electrical connections to the mapping electrodes 175. By way of example and not limitation, an embodiment of the distal insert is fabricated from stainless steel.

With respect to material, the exemplary electrode tip 110 may be formed from any suitable electrically conductive material. By way of example, but not limitation, suitable materials for the main portion of the electrode tip 110, e.g.

the side wall 125 and planar distal end 115, include silver, platinum, gold, stainless steel, plated brass, platinum iridium and combinations thereof. For example, some embodiments use a platinum-iridium alloy. Some embodiments use an alloy with approximately 90% platinum and 10% iridium. This conductive material is used to conduct RF energy used to form lesions during the ablation procedure. The distal insert 155 may be a thermal mass formed from any suitable electrically and thermally conducting material such as, for example, brass, copper and stainless steel. The distal insert 155 may, alternatively, be made of thermally conducting and electrically non-conducing materials.

The catheter systems 100, 200, 300 may be part of a mapping and ablation system that includes an open-irrigated catheter. The systems 100, 200, 300 may include an ablation electrode tip 110 with mapping electrodes 175 and irrigation ports 135. The catheter may be functionally divided into four regions: the operative distal probe assembly region (100, 200, 300), a main catheter region (not shown), a deflectable catheter region (not shown), and a proximal catheter handle region (not shown) where a handle assembly (not shown) is attached. The catheter body 105 includes a coolant conduit 140 and may include other tubular element(s) to provide the desired functionality to the catheter. The addition of metal in the form of a braided mesh layer (not shown) sandwiched in between layers of plastic tubing may be used to increase the rotational stiffness of the catheter.

A deflectable catheter region allows the catheter to be steered through the vasculature of the patient and allows the probe assembly to be accurately placed adjacent the targeted tissue region. A steering wire (not shown) may be slidably disposed within the catheter body. A handle assembly (not shown) may include a steering member such as a rotating steering knob that is rotatably mounted to the handle. Rotational movement of the steering knob relative to the handle in a first direction may cause a steering wire to move proximally relative to the catheter body which, in turn, tensions the steering wire, thus pulling and bending the catheter deflectable region into an arc; and rotational movement of the steering knob relative to the handle in a second direction may cause the steering wire to move distally relative to the catheter body which, in turn, relaxes the steering wire, thus allowing the catheter to return toward its form. To assist in the deflection of the catheter, the deflectable catheter region may be made of a lower durometer plastic than the main catheter region.

The system may include an RF generator (not shown) used to generate the energy for the ablation procedure. An RF generator may include a source for the RF energy and a controller for controlling the timing and the level of the RF energy delivered through the electrode tip 110. The system may include a fluid reservoir and pump (not shown) for pumping cooling fluid, such as a saline, through the catheter and out through the irrigation ports 135. A mapping signal processor (not shown) may be connected to the mapping electrodes 175. The mapping signal processor and mapping electrodes 175 detect electrical activity of the heart. This electrical activity is evaluated to analyze an arrhythmia and to determine where to deliver the ablation energy as a therapy for the arrhythmia. One of ordinary skill in the art will understand that, the modules and other circuitry shown and described herein can be implemented using software, hardware, and/or firmware. Various disclosed methods may be implemented as a set of instructions contained on a computer-accessible medium capable of directing a processor to perform the respective method. Additional details concerning this type of catheter system may be found in, for example, U.S. Publication Nos. 2008/0243214, 2009/0093810, 2010/0331658, and 2011/0009857, which are hereby incorporated by reference.

The materials that can be used for the various components of the open-irrigated ablation catheters disclosed herein may vary. For simplicity purposes, the following discussion makes reference to the catheter body 105. However, this is not intended to limit the devices and methods described herein, as the discussion may be applied to other similar tubular members and/or components of tubular members or devices disclosed herein.

Catheter body 105 and/or other components of catheter system 100 may be made from a metal, metal alloy, polymer (some examples of which are disclosed below), a shape memory polymer, a metal-polymer composite, ceramics, other composites, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties. Shape memory polymer materials may also be used for catheter body 105.

In at least some embodiments, portions or all of catheter body 105 may also be loaded with, made of, or otherwise include a radiopaque material. Radiopaque materials are understood to be materials capable of producing a relatively bright image on a fluoroscopy screen or another imaging technique during a medical procedure. This relatively bright image aids the user of catheter system 100 in determining its location. Some examples of radiopaque materials can include, but are not limited to, gold, platinum, palladium, tantalum, tungsten alloy, polymer material loaded with a radiopaque filler (e.g., barium sulfate, bismuth subcarbonate, etc.), and the like. Additionally, other radiopaque marker bands and/or coils may also be incorporated into the design of catheter system 100 to achieve the same result.

In some embodiments, a degree of Magnetic Resonance Imaging (MRI) compatibility is imparted into catheter system 100. For example, catheter body 105, or portions thereof, may be made of a material that does not substantially distort the image and create substantial artifacts (i.e., gaps in the image). Certain ferromagnetic materials, for example, may not be suitable because they may create artifacts in an MRI image. Catheter body 105, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of catheter body 105 that may define a generally smooth outer surface for catheter system 100. In other embodiments, however, such a sheath or covering may be absent from a portion of all of catheter system 100. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the catheter system 100 may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portions of catheter system 100. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. An open-irrigated ablation catheter system, comprising:
a catheter body with a distal end;
an electrode tip body with a distal end, a proximal end, and a longitudinal axis, the proximal end configured for connection to the distal end of the catheter body, the electrode tip body having a wall defining an open interior region, the wall having one or more irrigation ports, wherein the wall is conductive for delivering radio frequency (RF) energy, wherein the one or more irrigation ports are in fluid communication with the open interior region to allow fluid to flow from the open interior region through the one or more irrigation ports; and
a coolant conduit disposed within the catheter body, the coolant conduit having a fluid directing mechanism at a distal end thereof configured to direct fluid laterally towards the wall, the fluid directing mechanism including one or more side openings proximal of the distal end of the coolant conduit and further including surfaces that are angled acutely with respect to the longitudinal axis of the electrode tip body such that coolant flowing through the coolant conduit exits the one or more side openings at an angle towards the distal end of the catheter body.

2. The system of claim 1, wherein the distal end of the electrode tip body is closed and the proximal end of the electrode tip body is open, the system further comprising a distal insert positioned within the electrode tip body to separate the open interior region into a distal fluid reservoir and a proximal fluid reservoir, the distal insert having an opening connecting the distal and proximal fluid reservoirs.

3. The system of claim 2, wherein the one or more side openings in the coolant conduit are in fluid communication with the proximal fluid reservoir.

4. The system of claim 2, further comprising a thermocouple, wherein the distal insert includes a second opening therethrough to receive the thermocouple such that a distal end of the thermocouple is positioned in the distal fluid reservoir.

5. The system of claim 1, wherein the wall of the electrode tip body has an exterior surface with one or more side openings therein, the system further comprising one or more mapping electrodes positioned in the one or more side openings in the exterior surface of the wall.

6. The system of claim 1, wherein the coolant conduit includes two or more lumens.

7. The system of claim 1, wherein the distal end of the coolant conduit is closed.

8. The system of claim 1, wherein the distal end of the coolant conduit is open and extends distal of the distal end of the catheter body, wherein the fluid directing mechanism includes a blocking member spaced from the open distal end of the coolant conduit, wherein the blocking member extends transverse to a longitudinal axis of the coolant conduit, wherein the blocking member is positioned such that flow of fluid from the coolant conduit impacts the blocking member and is directed laterally towards the wall of the electrode tip body.

9. An open-irrigated turbulent flow catheter system, comprising:
a catheter body with a distal end; an electrode tip body with a distal end and a proximal end configured for connection to the distal end of the catheter body, the electrode tip body defining an open interior region and one or more irrigation ports, wherein the electrode tip body is conductive for delivering radio frequency (RF) energy;
a coolant conduit disposed within the catheter body, the coolant conduit having a distal end, the coolant conduit having one or more side openings therein proximal of the distal end, wherein the one or more side openings are angled proximally such that at least a portion of coolant flowing through the coolant conduit is directed towards the proximal end of the electrode tip body; and
a distal insert positioned within the electrode tip body and separating the open interior region into a distal fluid reservoir and a proximal fluid reservoir, wherein the entire distal insert is spaced apart from and positioned distally from the distal end of the coolant conduit, wherein the distal end of the coolant conduit is positioned in the proximal fluid reservoir, the distal insert having an opening connecting the distal and proximal fluid reservoirs, wherein the one or more irrigation ports are disposed in the distal fluid reservoir.

10. The system of claim 9, wherein the distal end of the coolant conduit extends distal of the distal end of the catheter body, within the open interior region.

11. The system of claim 9, wherein the distal end of the electrode tip body is closed and the proximal end of the electrode tip body is open.

12. The system of claim 9, further comprising a thermocouple, wherein the distal insert includes a second opening therethrough to receive the thermocouple such that a distal end of the thermocouple is positioned in the distal fluid reservoir.

13. The system of claim 9, wherein the electrode tip body has an exterior surface with openings therein, the system further comprising mapping electrodes positioned in the openings in the exterior surface.

14. The system of claim 9, wherein the coolant conduit includes two or more lumens, each lumen having a distal end and one or more side openings proximal of the distal end.

15. The system of claim 9, wherein the distal end of the coolant conduit is closed.

16. The system of claim 9, wherein the electrode tip body has a circumferential wall, and wherein the distal insert has an exterior surface at least a portion of which is directly coupled to the circumferential wall.

17. An open-irrigated ablation catheter system, comprising:
- a catheter body;
- an electrode tip body with a distal end and a proximal end configured for connection to a distal end of the catheter body, the electrode tip body having a wall defining an open interior region, the wall having one or more irrigation ports in fluid communication with the open interior region, wherein the wall is conductive for delivering radio frequency (RF) energy;
- a coolant conduit disposed within the catheter body, an open distal end of the coolant conduit extending distal of the distal end of the catheter body;
- a blocking member spaced from the open distal end of the coolant conduit, the blocking member configured to interrupt and divert distal flow of fluid from the coolant conduit; and
- a distal insert positioned within the electrode tip body separating the open interior region into a distal fluid reservoir and a proximal fluid reservoir, wherein the blocking member is positioned within the proximal fluid reservoir.

18. The system of claim 17, wherein the blocking member is a plate extending transverse to a longitudinal axis of the coolant conduit, wherein flow of fluid from the coolant conduit impacts the plate and is directed towards the wall of the electrode tip body.

19. The system of claim 18, wherein the plate extends radially beyond the coolant conduit.

* * * * *